United States Patent
Sinha et al.

(10) Patent No.: US 11,267,790 B2
(45) Date of Patent: Mar. 8, 2022

(54) PROCESSES FOR PREPARING PLASMA KALLIKREIN INHIBITORS

(71) Applicants: Rezolute, Inc., Redwood City, CA (US); ActiveSite Pharmaceuticals, Inc., San Francisco, CA (US)

(72) Inventors: Sukanto Sinha, San Francisco, CA (US); Tamie Chilcote, San Francisco, CA (US); Baburaj Krishnan, Bangalore (IN); Ganapati Bhat, Bangalore (IN); Vineet Malik, Bangalore (IN)

(73) Assignees: Rezolute, Inc., Redwood City, CA (US); ActiveSite Pharmaceuticals, Inc., San Francisco, CA (US)

( * ) Notice: Subject to any disclaimer, the term of this patent is extended or adjusted under 35 U.S.C. 154(b) by 0 days.

(21) Appl. No.: 16/922,080

(22) Filed: Jul. 7, 2020

(65) Prior Publication Data
US 2021/0009526 A1    Jan. 14, 2021

Related U.S. Application Data

(60) Provisional application No. 62/871,526, filed on Jul. 8, 2019.

(51) Int. Cl.
 C07D 231/14        (2006.01)
 C07D 307/68        (2006.01)
     (Continued)

(52) U.S. Cl.
 CPC .........  C07D 231/14 (2013.01); C07D 207/34 (2013.01); C07D 249/04 (2013.01);
     (Continued)

(58) Field of Classification Search
 None
 See application file for complete search history.

(56) References Cited

U.S. PATENT DOCUMENTS

| 4,166,452 A | 9/1979 | Generales |
| 4,256,108 A | 3/1981 | Theeuwes |

(Continued)

FOREIGN PATENT DOCUMENTS

| WO | 9013332 A1 | 11/1990 |
| WO | 9112779 A1 | 9/1991 |

(Continued)

OTHER PUBLICATIONS

International Search Report and Written Opinion for International PCT Application No. PCT/US2020/040958, dated Jan. 14, 2017 (7 pages).

(Feb. 5, 1994) "Indications for Fibrinolytic Therapy in Suspected Acute Myocardial Infarction: Collaborative Overview of Early Mortality and Major Morbidity Results From All Randomised Trials of More Than 1000 Patients. Fibrinolytic Therapy Trialists' (FTT) Collaborative", The Lancet, 343(8893):311-322.

Banerji et al. (Feb. 23, 2017) "Inhibiting Plasma Kallikrein for Hereditary Angioedema Prophylaxis", The New England Journal of Medicine, 376(8):717-728.

Bates et al. (Jul. 26, 2005) "Coagulation Assays", Circulation, 112:e53-e60.

Bender et al. (Sep. 15, 2017) "Factor Xii-driven Inflammatory Reactions With Implications for Anaphylaxis", Frontiers in Immunology, 8:1115 (11 pages).

Berge et al. (Jan. 1977) "Pharmaceutical Salts", Journal of Pharmaceutical Sciences, 66(1):1-19.

(Continued)

*Primary Examiner* — Samantha L Shterengarts
(74) *Attorney, Agent, or Firm* — Mintz, Levin, Cohn, Ferris, Glovsky and Popeo, P.C.

(57) ABSTRACT

A process for preparing and purifying a compound of Formula I is provided:

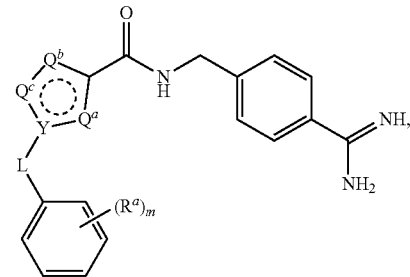

(Formula I)

or a salt thereof, wherein the subscript m is an integer of from 0 to 3;
each $R^a$ is independently selected from the group consisting of $(C_3-C_8)$cycloalkyl, $(C_1-C_4)$haloalkyl, halogen, —OH, —OR$^1$, —SH, —SR$^1$, —S(O)R$^1$, —S(O)$_2$R$^1$, —SO$_2$NH$_2$, —C(O)NH$_2$, —C(O)NHR$^1$, —C(O)N(R$^1$)$_2$, —C(O)R$^1$, —C(O)H, —CO$_2$R$^1$, —NO$_2$, —NH$_2$, —NHR$^1$, —N(R$^1$)$_2$, wherein each $R^1$ is independently $(C_1-C_8)$alkyl;

L is a linking group selected from the group consisting of a bond or CH$_2$;

$Q^a$, $Q^b$, and $Q^c$ are each members independently selected from the group consisting of N, S, O and C(R$^q$) wherein each $R^q$ is independently selected from the group consisting of H, $C_{1-8}$ alkyl, halo and phenyl, and the ring having $Q^a$, $Q^b$, $Q^c$ and Y as ring vertices is a five-membered ring having two double bonds; and Y is selected from the group consisting of C and N.

20 Claims, No Drawings

(51) Int. Cl.
C07D 277/56 (2006.01)
C07D 207/34 (2006.01)
C07D 333/38 (2006.01)
C07D 249/04 (2006.01)

(52) U.S. Cl.
CPC ......... C07D 277/56 (2013.01); C07D 307/68 (2013.01); C07D 333/38 (2013.01)

(56) References Cited

U.S. PATENT DOCUMENTS

| | | | |
|---|---|---|---|
| 4,265,874 | A | 5/1981 | Bonsen et al. |
| 4,733,655 | A | 3/1988 | Smal |
| 4,800,882 | A | 1/1989 | Gianturco |
| 4,886,062 | A | 12/1989 | Wiktor |
| 5,102,417 | A | 4/1992 | Palmaz |
| 5,419,760 | A | 5/1995 | Narciso, Jr. |
| 5,429,634 | A | 7/1995 | Narciso, Jr. |
| 6,770,729 | B2 | 8/2004 | Van |
| 8,258,170 | B2 | 9/2012 | Sinha et al. |
| 8,658,685 | B2 | 2/2014 | Aiello et al. |
| 8,691,861 | B2 | 4/2014 | Sinha et al. |
| 2002/0012680 | A1 | 1/2002 | Patel et al. |
| 2002/0037857 | A1 | 3/2002 | Semple et al. |
| 2004/0243225 | A1 | 12/2004 | Ragheb et al. |
| 2013/0296245 | A1 | 11/2013 | Li et al. |

FOREIGN PATENT DOCUMENTS

| | | |
|---|---|---|
| WO | 2006066878 A1 | 6/2006 |
| WO | 2008016883 A2 | 2/2008 |
| WO | 2021007190 A1 | 1/2021 |

OTHER PUBLICATIONS

Brodie et al. (Jul. 1994) "Six-month Clinical and Angiographic Follow-up After Direct Angioplasty for Acute Myocardial Infarction. Final Results From the Primary Angioplasty Registry", Circulation, 25:156-162.

Clermont et al. (May 2011), "Plasma Kallikrein Mediates Retinal Vascular Dysfunction and Induces Retinal Thickening in Diabetic Rats", Diabetes, 60(5): 1590-1598.

Davie et al. (Sep. 18, 1964) "Waterfall Sequence for Intrinsic Blood Clotting", Science,145(3638):1310-1312.

Ewald et al. (Jan. 1, 1995) "Plasmin-mediated Activation of Contact System in Response to Pharmacological Thrombolysis", Circulation, 91(1):28-36.

Hathaway et al. (Nov. 1965) "Evidence for a New Plasma Thromboplastin Factor. I. Case Report, Coagulation Studies and Physicochemical Properties", Blood, 26(5):521-532.

Hoffmeister et al. (Dec. 8, 1998) "Thrombolytic Therapy in Acute Myocardial Infarction: Comparison of Procoagulant Effects of Streptokinase and Alteplase Regimens With Focus on the Kallikrein System and Plasmin", Circulation, 98(23):2527-2533.

Joseph et al. (2005) "Formation of Bradykinin: a Major Contributor to the Innate Inflammatory Response", Advances in Immunology, 86:159-208.

Keeley et al. (Jan. 4, 2003) "Primary Angioplasty Versus Intravenous Thrombolytic Therapy for Acute Myocardial Infarction: a Quantitative Review of 23 Randomised Trials", The Lancet, 361(9351):13-20.

Kou et al. (Jan. 2006) "Unstable Angina and Non-ST-segment Myocardial Infarction: an Evidence-based Approach to Management", Mount Sinai Journal of Medicine, 73(1 ):449-468.

Lawrie et al. (Jun. 1998) "Assessment of Actin FS and Actin FSL Sensitivity to Specific Clotting Factor Deficiencies", Clinical & Laboratory Haematology, 20(3):179-186.

MacFarlane Rg. (May 2, 1964) "An Enzyme Cascade in the Blood Clotting Mechanism, and Its Function as a Biochemical Amplifier", Nature, 202(4931):498-499.

Li et al. (Oct. 12, 2018) "Prevention of Acute Liver Injury by Suppressing Plasma Kallikrein-dependent Activation of Latent TGF-β", Biochemical and Biophysical Research Communications, 504(4):857-864.

Menon et al. (Sep. 2004) "Thrombolysis and Adjunctive Therapy in Acute Myocardial Infarction: the Seventh Accp Conference on Antithrombotic and Thrombolytic Therapy", Chest, 126(3 Suppl):549S-575S.

Phipps etaL (Feb. 2009) "Plasma Kallikrein Mediates Angiotensin II Type 1 Receptor-stimulated Retinal Vascular Permeability", Hypertension, 53(2):175-181.

Aygören-Pürsün et al. (Jul. 26, 2018) "Oral Plasma Kallikrein Inhibitor for Prophylaxis in Hereditary Angioedema", The New England Journal of Medicine, 379(4):352-362.

Ratnoff et al. (Apr. 1955) "A Familial Hemorrhagic Trait Associated With a Deficiency of a Clot-promoting Fraction of Plasma", Journal of Clinical Investigation, 34(4):602-613.

Rosen et al. (Nov. 20, 1997) "Mice Lacking Factor Vii Develop Normally but Suffer Fatal Perinatal Bleeding", Mature, 390(6657):290-294.

Simao et al. (Apr. 20, 2017) "Plasma Kallikrein Mediates Brain Hemorrhage and Edema Caused by Tissue Plasminogen Activator Therapy in Mice After Stroke", Blood, 129(16):2280-2290.

Stone et al. (Mar. 30, 1999) "Clinical and Angiographic Follow-up After Primary Stenting in Acute Myocardial nfarction: the Primary Angioplasty in Myocardial Infarction (Pami) Stent Pilot Trial", Circulation, 99(12): 1548-1554.

Tamai et al. (Mar. 2004) "Frequency and Time Course of Reocclusion and Restenosis in Coronary Artery Occlusions After Balloon Angioplasty Versus Wiktor Stent Implantation: Results From the Mayo-japan Investigation for Chronic Total Occlusion (Majic) Trial", American Heart Journal, 147(3):E9 (7 pages).

Verheugt et al. (Mar. 15, 1996) "Reocclusion: the Flip Side of Coronary Thrombolysis", Journal of the American College of Cardiology, 27(4):766-773.

Wang et al. (Jul. 2016) "Plasma Kallikrein-kinin System Mediates Immune-mediated Renal Injury in Trichloroethylene-sensitized Mice", Journal of Immunotoxicology, 13(4):567-579.

Zijlstra et al. (Mar. 11, 1993) "A Comparison of Immediate Coronary Angioplasty With Intravenous Streptokinase in Acute Myocardial Infarction", The New England Journal of Medicine, 328(10):680-684.

PROCESSES FOR PREPARING PLASMA KALLIKREIN INHIBITORS

FIELD OF THE INVENTION

This invention relates to processes for preparing and purifying plasma kallikrein inhibitors, and compounds useful in those processes.

BACKGROUND OF THE INVENTION

Thrombus formation is essential for preventing blood loss and allowing repair of an injured vessel, a process known as hemostasis, yet a thrombus can also be pathologic when it occludes a blood vessel depriving tissue of oxygen. The occlusion of an artery by a thrombus, arterial thrombosis, most often occurs at the site of a ruptured or eroded atherosclerotic plaque (V. Kou et al., Mt Sinai J Med (2006) 73:449-68). Specific occlusion of the coronary arteries results in acute coronary syndrome which includes unstable angina and myocardial infarction (MI).

A fibrin clot may be produced in blood by initiation of one of two distinct routes, the intrinsic and extrinsic pathways, which converge onto a common pathway of coagulation (R. G. Macfarlane, Nature (1964) 202:498-99; E. W. Davie et al., Science (1964) 145:1310-12; K. Joseph et al., Adv Immunol (2005) 86:159-208). Experimental data have suggested both PK- and FXII-deficient individuals have severely impaired intrinsic pathway-mediated clot formation despite their lack of bleeding phenotype (O. D. Ratnoff et al., J Clin Invest (1955) 34:602-13; R. W. Colman, (2001) in "Hemostasis and Thrombosis: Basic principles and clinical practice" (R. W. Colman et al. eds., Lippincott Williams & Wilkins, Philadelphia, Pa., pp. 103-122); E. D. Rosen et al., Nature (1997) 390:290-94; W. E. Hathaway et al., Blood (1965) 26:521-32; A. S. Lawrie et al., Clin Lab Haematol (1998) 20:179-86; and S. M. Bates et al., Circulation (2005) 112:53-60). In the intrinsic pathway, by binding to the surface, a small amount of factor XII (FXII) is activated (FXIIa) which in turn activates plasma kallikrein (PK) through proteolysis. Importantly, PK then generates additional FXIIa in a feedback loop which in turn activates factor XI (FXI) to FXIa to connect to the common pathway. Although the initial activation of the intrinsic pathway is through a small amount of FXIIa activating a small amount of PK, it is the subsequent feedback activation of FXII by PK that controls the extent of activation of the intrinsic pathway and hence downstream coagulation (W. E. Hathaway et al., Blood (1965) 26:521-32).

Current treatment for acute MI or ischemic stroke in a hospital setting requires emergency measures to dissolve the occluding thrombus and allow reperfusion (restored blood flow). One of the common ways of doing this is by treating the patients with fibrinolytic agents, such as tissue plasminogen activator (t-PA) or streptokinase, agents that lead to the generation of active plasmin from plasminogen. Plasmin cleaves the fibrin meshwork of the thrombus, therefore leading to clot dissolution. Such fibrinolytic agents are the most frequently used treatment for reperfusion worldwide. However, fibrinolysis is also associated with a high degree of re-thrombosis with subsequent rates of reocclusion of up to 50% depending on the study (F. Zijlstra et al., N Engl J Med (1993) 328:680-84; B. R. Brodie et al., Circulation (1994) 90:156-62; G. W. Stone et al., Circulation (1999) 99:1548-54; H. Tamai et al., Am Heart J (2004) 147:E9; F. W. Verheugt et al., J Am Coll Cardiol (1996) 27:766-73).

Patients who have undergone acute MI show clinical evidence of being in a hypercoagulable (clot-promoting) state. This hypercoagulability is paradoxically additionally aggravated in those receiving fibrinolytic therapy. Increased generation of thrombin, as measured by thrombin-antithrombin III (TAT) levels up to 2-fold higher, is observed in patients undergoing such treatment compared to the already high levels observed in those receiving heparin alone (H. M. Hoffmeister et al., Circulation (1998) 98:2527-33). The increase in thrombin has been proposed to result from plasmin-mediated activation of the intrinsic pathway. Plasmin-mediated activation of the intrinsic pathway system is known to occur in blood (G. A. Ewald et al., Circulation (1995) 91:28-36), and it has been suggested that this occurs as a consequence of direct activation of FXII by plasmin.

Not only does the fibrinolysis-induced hypercoagulability lead to increased rates of reocclusion, it is also probably responsible, at least in part, for failure to achieve complete fibrinolysis of the clot, a major shortcoming of fibrinolytic therapy (E. C. Keeley et al., Lancet (2003) 361:13-20). Another problem in fibrinolytic therapy is the accompanying 3-fold elevated risk of intracranial hemorrhage (ICH) (V. Menon et al., Chest (2004) 126:549S-575S; Fibrinolytic Therapy Trialists' Collaborative Group, Lancet (1994) 343: 311-22). Hence, an adjunctive anti-coagulant therapy that does not increase the risk of bleeding, but inhibits the formation of new thrombin, would be greatly beneficial.

It has been found that treatment of wild-type mice with an irreversible inhibitor of FXII led to fewer occluded vessels and less ischemic cortical damage and inhibition of FXII, would be protective for arterial thrombosis, such as that occurring during acute MI or during thrombotic stroke (WO/2006 066878). However, peptidic drugs have numerous shortcomings including limited application to acute studies because of short half-lives, i.v. administration requiring medical intervention, and the development of anti-peptide antibodies by patients undergoing treatment.

Plasma kallikrein has also been implicated in diabetic macular edema and retinopathy (A. Clermont et al., Diabetes (2011) 60:1590-98; J. A. Phipps et al., Hypertension (2009) 53:175-81); hereditary angioedema with C1 inhibitor deficiency (A. Banerji et al., N Engl J Med (2017) 376:717-28; E. Aygören-Pürsün et al., N Engl J Med (2018) 379 (4):352-62); acute liver injury (M. Li et al., Biochem Biophys Res Commun (2018) 504 (4):857-64); inflammation and anaphylaxis (L. Bender et al., Front Immunol (2017) 8:1115); exacerbation of hemorrhagic transformation and cerebral edema after treatment with recombinant tissue plasminogen activator (tPA) (F. Simão et al., Blood (2017) 129 (16):2280-90); and chemical-sensitized renal damage (H. Wang et al., J Immunotoxicol (2016) 13 (4):567-79).

Suitable plasma kallikrein inhibitors have been developed (Sinha et al., WO2008/016883; U.S. Pat. No. 8,258,170). However, manufacturing processes for such compounds remain an unmet need.

BRIEF SUMMARY OF THE INVENTION

We have now invented new processes of preparing the compounds of Sinha et al., (U.S. Pat. No. 8,258,170, incorporated herein by reference in full), as well as novel intermediates, and a novel purification process, that provide the plasma kallikrein inhibitors of Sinha et al. in suitable form for pharmaceutical use.

DETAILED DESCRIPTION OF THE INVENTION

Definitions

Unless otherwise stated the following terms used in the specification and claims have the meanings given below.

The term "alkyl", by itself or as part of another substituent, means, unless otherwise stated, a straight or branched chain hydrocarbon radical, having the number of carbon atoms designated (i.e., $C_1$-$C_8$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl), when a prefix is not included to indicate the number of main chain carbon atoms in an alkyl portion, the radical or portion thereof will have 12 or fewer main chain carbon atoms.

The term "alkylene" by itself or as part of another substituent means a divalent radical derived from an alkane, as exemplified by —$CH_2CH_2CH_2CH_2$—. Typically, an alkyl (or alkylene) group will have from 1 to 12 carbon atoms. A "lower alkyl" or "lower alkylene" is a shorter chain alkyl or alkylene group, generally having six or fewer carbon atoms.

The term "cycloalkyl" refers to hydrocarbon rings having the indicated number of ring atoms (e.g., ($C_3$-$C_8$)cycloalkyl) and being fully saturated or having no more than one double bond between ring vertices. One or two C atoms may optionally be replaced by a carbonyl. "Cycloalkyl" also includes bicyclic and polycyclic hydrocarbon rings such as, for example, bicyclo[2.2.1]heptane, bicyclo[2.2.2]octane, and the like. When a prefix is not included to indicate the number of ring carbon atoms in a cycloalkyl, the radical or portion thereof will have 8 or fewer ring carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Thus, a group represented as "—$NR^aR^b$" includes piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "($C_1$-$C_4$) haloalkyl" is mean to include trifluoromethyl, 2,2,2-trifluoroethyl, 4-chlorobutyl, 3-bromopropyl, and the like.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropyl-amine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, S. M. Berge et al., *J Pharm Sci* (1977) 66:1-19). Certain specific compounds of the present invention contain both basic and acidic functionalities that allow the compounds to be converted into either base or acid addition salts. The term "pharmaceutically acceptable" is meant the carrier, diluent or excipient must be compatible with the other ingredients of the formulation and not deleterious to the recipient thereof.

The term "composition" as used herein is intended to encompass a product comprising the specified ingredients in the specified amounts, as well as any product which results, directly or indirectly, from combination of the specified ingredients in the specified amounts.

General

The compounds of Formula I prepared by the processes of the invention are useful as plasma kallikrein (PK) inhibitors, for the prevention and treatment of blood coagulation, such as thrombosis, and PK-dependent diseases and conditions. For example, the compounds inhibit the formation of thrombin by the intrinsic pathway and thus reduce the risk of new pathogenic thrombus formation (reocclusion), and also improve fibrinolytic-induced reperfusion when given as adjunctive therapy with a fibrinolytic regimen. Compounds of Formula I are also useful for treating other disease and disorders that are mediated by plasma kallikrein, such as diabetic macular edema, diabetic retinopathy, hereditary angioedema with C1 inhibitor deficiency, acute liver injury, inflammation and anaphylaxis, exacerbation of hemorrhagic transformation and cerebral edema after treatment with recombinant tissue plasminogen activator (tPA), and chemical-sensitized renal damage.

Methods of Preparing Compounds of Formula I

The Compounds of Formula I

Compounds of Formula I are made by the processes of the current invention:

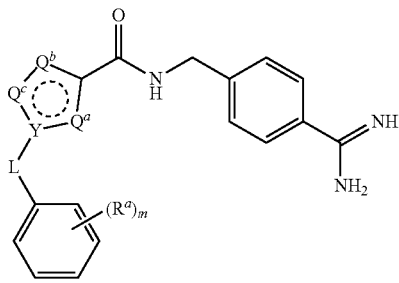

(Formula I)

wherein the subscript m is an integer of from 0 to 3;
each $R^a$ is independently selected from the group consisting of $(C_3$-$C_8)$cycloalkyl, $(C_1$-$C_4)$haloalkyl, halogen, —OH, —$OR^1$, —SH, —$SR^1$, —$S(O)R^1$, —$S(O)_2R^1$, —$SO_2NH_2$, —$C(O)NH_2$, —$(O)NHR^1$, —$C(O)N(R^1)_2$, —$C(O)R^1$, —$C(O)H$, —$CO_2H$, —$CO_2R^1$, —$NO_2$, —$NH_2$, —$NHR^1$, —$N(R^1)_2$, wherein each $R^1$ is independently $(C_1$-$C_8)$alkyl;
L is a linking group selected from the group consisting of a bond or $CH_2$;
$Q^a$, $Q^b$, and $Q^c$ are each members independently selected from the group consisting of N, S, O and $C(R^q)$ wherein each $R^q$ is independently selected from the group consisting of H, $C_{1-8}$ alkyl, halo and phenyl, and the ring having $Q^a$, $Q^b$, $Q^c$ and Y as ring vertices is a five-membered ring having two double bonds; and
Y is selected from the group consisting of C and N;
and pharmaceutically acceptable salts thereof.

In some embodiments, Y is N and $Q^a$, $Q^b$, and $Q^c$ are each independently $C(R^q)$. In some embodiments, each $R^q$ is methyl. In some embodiments, $Q^b$ is CH, and $Q^a$ and $Q^c$ are each C—$CH_3$. In some embodiments, Y and $Q^c$ are each N, and $Q^a$ and $Q^b$ are each independently $C(R^q)$. In some embodiments, Y and $Q^b$ are each N, and $Q^a$ and $Q^c$ are each independently $C(R^q)$. In some embodiments, Y and $Q^b$ are each N, and $Q^a$ and $Q^c$ are each C—H. In some embodiments, L is —$CH_2$—, m is 0, 1, or 2, and each $R^a$ is independently halo.

In some embodiments, the compound of Formula I is one of:

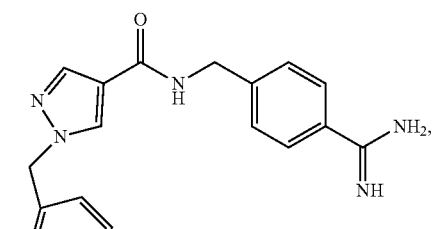

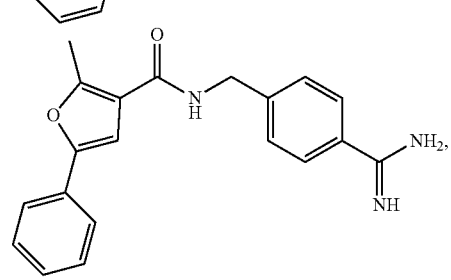

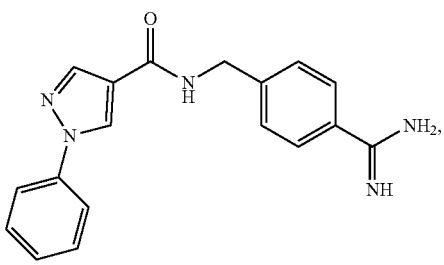

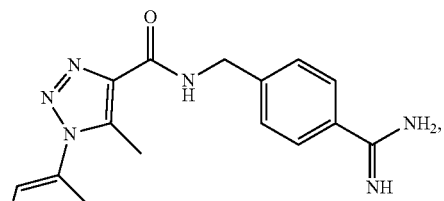

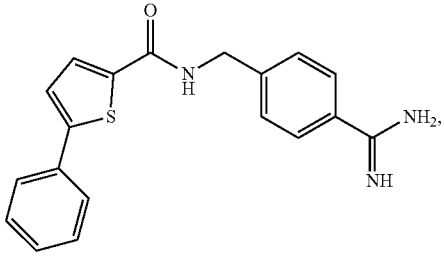

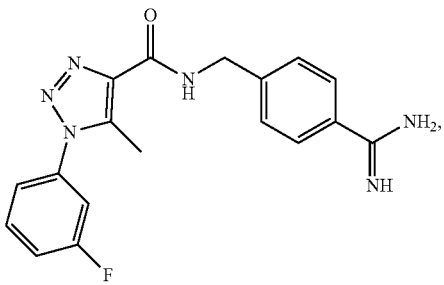

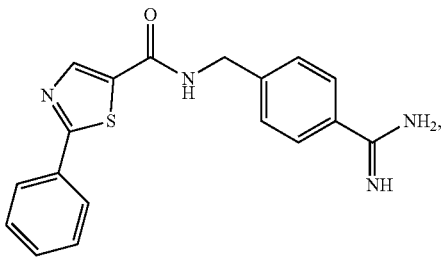

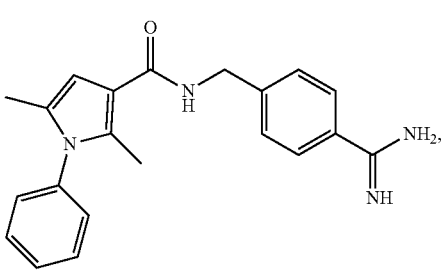

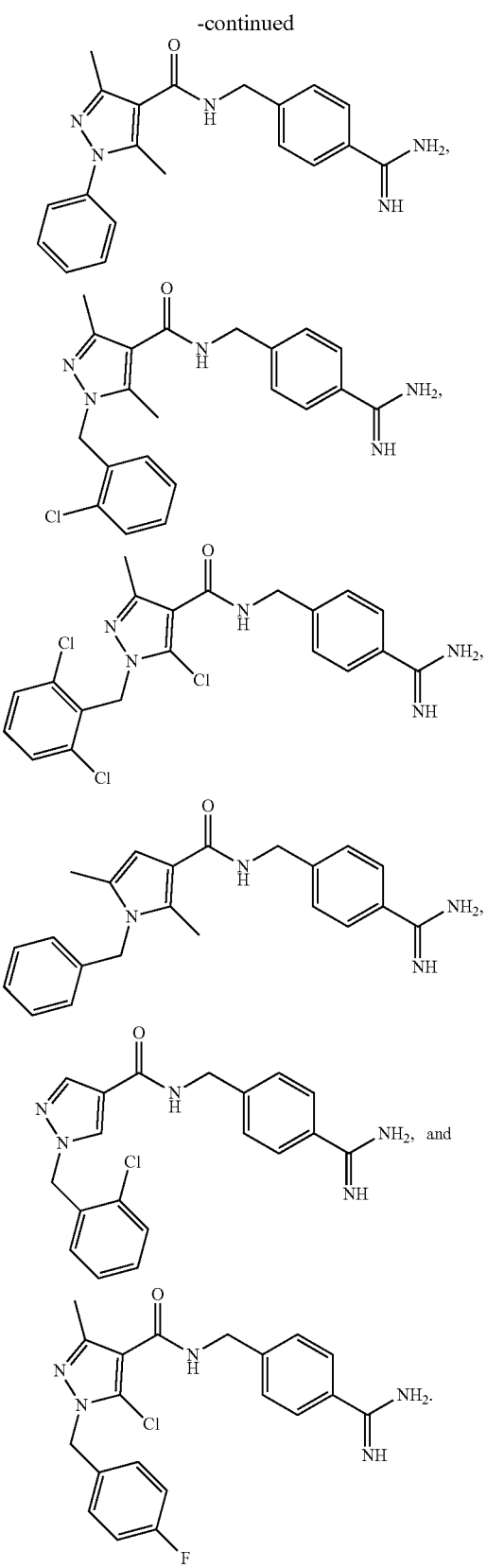

In some embodiments, the compound of Formula I is 1-benzyl-N-(4-carbamimidoyl-benzyl)-1H-pyrazole-4-carboxamide, or a pharmaceutically acceptable salt thereof.

Method of Preparation

The process of the invention has been optimized for yield and purity to a degree sufficient for commercialization. Compounds of Formula IV are obtained from commercial sources, or are prepared by methods known in the art from precursor compounds that are commercially available.

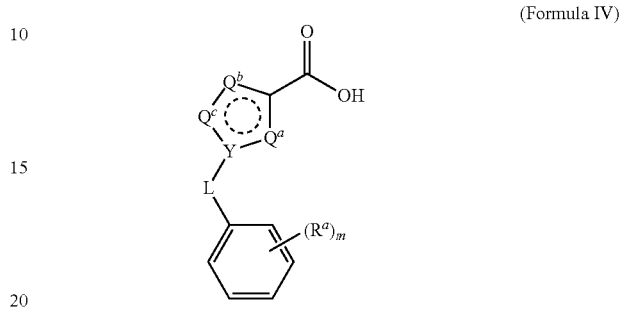

(Formula IV)

For example, compounds of Formula IV wherein Y is N and L is —CH$_2$— may be prepared from precursors of Formula V:

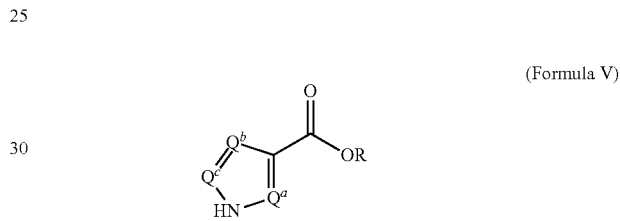

(Formula V)

by contacting the compound of Formula V with a suitably substituted benzyl halide (for example benzyl bromide) in an aprotic solvent in the presence of a strong base, followed by hydrolysis of the ester. For example, ethyl 1H-pyrazole-3-carboxylate is treated with K$_2$CO$_3$ in acetone, followed by benzyl bromide to produce the compound of Formula IV, ethyl 1-benzyl-1H-pyrazole-3-carboxylate. The ethyl ester is then treated with, for example, KOH in methanol to provide the free acid. Other heterocycles may be substituted in the compound of Formula V to provide 1-benzyl derivatives of imidazole, triazole, thiazole, thiadiazaole, and the like. Similarly, substituted benzyl halides such as 2-chlorobenzyl bromide, 2,6-dichlorobenzyl bromide, 4-fluorobenzyl bromide, and 4-bromobenzyl bromide may be substituted for benzyl bromide to provide the corresponding compounds of Formula IV.

A. Process 1:

(A) The compound of Formula IV is then coupled with 4-aminomethylbenzonitrile using 1-propanephosphonic acid cyclic anhydride (T3P®) and triethylamine (Et$_3$N) in an aprotic solvent to produce the compound of Formula III. In some embodiments, the T3P® is provided as a 50% solution in ethyl acetate. The compound of Formula IV and the 4-aminomethyl-benzonitrile can be provided in about equimolar amounts, or one of the reactants can be provided in an excess ranging from about 0.2 to about 5 equivalents compared to the other reactant. In some embodiments, the ratio of the compound of Formula IV to 4-aminomethylbenzonitrile is from about 0.2 to about 5, from about 0.5 to about 2, from about 0.9 to about 1.2, or about 1.0.

The T3P® can be provided in a range of ratios as well. In some embodiments, the ratio of T3P® to the compound of Formula IV can be from about 0.5 to about 5, from about 0.8 to about 4, from about 1.0 to about 3, from about 1.2 to about 2.0, and from about 1.2 to about 1.8.

The triethylamine can also be provided in a range of ratios to the compound of Formula IV. In some embodiments, the ratio of Et$_3$N to the compound of Formula IV is from about 0.5 to about 10, from about 1 to about 8, from about 2 to about 5, and from about 3 to about 5.

In some embodiments, the aprotic solvent can be dichloromethane (DCM), tetrahydrofuran (THF), methyl ethyl ketone (MEK), dimethylsulfoxide (DMSO), ethyl acetate (EtOAc), methyl t-butyl ether (MTBE), and mixtures thereof. In some embodiments, the aprotic solvent is DCM.

The reaction is conducted in a temperature range in which the selected solvent is liquid. In some embodiments, the reaction temperature is from about 0° C. to about 100° C. In some embodiments, the reaction temperature is from about 15° C. to about the reflux temperature of the selected aprotic solvent. In some embodiments, the reaction temperature is from about 20° C. to about 80° C. In some embodiments, the reaction temperature is from about 20° C. to about 30° C.

The reaction time is in general the length of time required for the reaction to go substantially to completion, which may vary with the particular reactants, aprotic solvent, and reaction temperature selected. In some embodiments, the reaction time is about 30 minutes to about 48 hours. In some embodiments, the reaction time is about 1 hour to about 24 hours. In some embodiments, the reaction time is about 4 hours to about 12 hours. In some embodiments, the reaction time is about 6 hours to about 10 hours. In some embodiments, the reaction time is about 8 hours.

In some embodiments, the reaction is conducted under an inert atmosphere or anhydrous conditions. In some embodiments, the reaction is conducted under nitrogen.

(B) The compound of Formula III is then purified by extraction. In general, (i) the aprotic solvent containing the compound of Formula III is combined with water, (ii) mixed well (e.g., by stirring or shaking), (iii) the organic and aqueous layers allowed to separate, (iv) the aqueous layer is removed, and (v) the organic layer is dried to remove water. These steps, together or individually, may be repeated one, two, or three or more times. Further, the water may also contain salts, such as NaCl, NaHCO$_3$, and the like. The aqueous layers may also be extracted with an organic solvent, for example with DCM, and that organic solvent can be combined with the other organic layers obtained. The organic layer may then be dried over a suitable drying agent, such as sodium sulfate.

In some embodiments, the compound of Formula III in DCM is stirred with water, and the layers separated, then stirred with 10% aqueous NaHCO$_3$, separated, then saturated aqueous NaCl, and separated, followed by drying over Na$_2$SO$_4$. In some embodiments, the dried organic layer is then concentrated under reduced pressure, and taken up in acetone, washed with water, filtered, suction dried, and vacuum dried (or dried under reduced pressure) to provide purified compound of Formula III. The drying steps may be performed at elevated temperatures, for example above about 25° C., above about 30° C., above about 35° C., above about 40° C., above about 45° C., above about 50° C., above about 55° C., and above about 60° C. The drying temperature is generally lower than the melting temperature of the compound of Formula III, and can be lower than about 150° C., lower than about 120° C., lower than about 100° C., lower than about 90° C., lower than about 80° C., lower than about 75° C., lower than about 70° C., and lower than about 65° C.

B. Process 2:

(A) The compound of Formula III is then contacted with hydroxyl amine (NH$_2$OH) or a salt thereof in the presence of a weak base, in a suitable solvent, to provide a compound of Formula II. In some embodiments, the hydroxylamine is hydroxylamine hydrochloride. The hydroxylamine or hydroxylamine salt is added to the reaction in a ratio to the compound of Formula II of about 10 to about 0.5.

In some embodiments, the ratio of NH$_2$OH or salt to Formula II is about 10, about 9, about 8, about 7, about 6, about 5, about 4, about 3, about 2, or about 1. In some embodiments, the ratio is at least about 0.5, about 1, about 2, or about 3.

In some embodiments, the weak base is triethylamine or di-isopropylamine. The weak base is added to the reaction in a ratio to the compound of Formula II of about 10 to about 0.5. In some embodiments, the ratio of weak base to Formula II is about 10, about 9, about 8, about 7, about 6, about 5, about 4, about 3, about 2, or about 1. In some embodiments, the ratio is at least about 0.5, about 1, about 2, or about 3.

In some embodiments, the solvent is ethanol, isopropanol, methanol, DCM, EtOAc, or mixtures thereof. In some embodiments, the reaction temperature is elevated, for example above about 25° C., above about 30° C., above about 35° C., above about 40° C., above about 45° C., above about 50° C., above about 55° C., above about 60° C., above about 65° C., and above about 70° C. The reaction temperature is generally at or lower than the reflux temperature of the selected solvent, and can be lower than about 120° C., lower than about 100° C., lower than about 90° C., lower than about 80° C., lower than about 75° C., lower than about 70° C., and lower than about 65° C.

The reaction time is in general the length of time required for the reaction to go substantially to completion, which may vary with the particular reactants, aprotic solvent, and reaction temperature selected. In some embodiments, the reaction time is about 30 minutes to about 48 hours. In some embodiments, the reaction time is about 1 hour to about 24 hours. In some embodiments, the reaction time is about 4 hours to about 12 hours. In some embodiments, the reaction time is about 6 hours to about 10 hours. In some embodiments, the reaction time is about 7 hours.

(B) The compound of Formula II solution is then (i) concentrated, (ii) the compound precipitated by adding water, (iii) the solids are filtered, (iv) washed, and (v) dried to provide a purified compound of Formula II. In some embodiments, (i) concentration is effected by heating the solution containing the compound of Formula II, by reducing the pressure, or both. In some embodiments, the solution is concentrated by heating under reduced pressure to a volume of about 20% of the volume of the reaction mixture. Water (ii) is then added to the concentrated solution, and the mixture is stirred to precipitate solid compound of Formula II. The resulting solids are (iii) filtered, (iv) washed with water, and (v) dried.

In some embodiments, the solids are dried by suction filtration, drying under reduced pressure, drying at elevated temperature, or a combination thereof. In some embodiments, the solids are first dried by suction filtration, then by drying at elevated temperature under reduced pressure to provide purified compound of Formula II.

C. Process 3:

(A) The compound of Formula II is then subjected to reducing conditions in a protic solvent at an elevated temperature to provide a crude compound of Formula I. In some embodiments, the reducing conditions comprise catalytic hydrogenation. In some embodiments, the catalytic hydrogenation uses Raney nickel and hydrogen. In some embodiments, the protic solvent is acetic acid. This process may provide the compound of Formula I as an acetate salt.

In some embodiments, the elevated reaction temperature is above about 30° C., above about 35° C., above about 40° C., above about 45° C., above about 50° C., above about 55° C., and above about 60° C. The reaction temperature is generally at or lower than the reflux temperature of the solvent, and is lower than about 120° C., lower than about 100° C., lower than about 90° C., lower than about 80° C., lower than about 75° C., lower than about 70° C., lower than about 65° C., lower than about 60° C., and lower than about 55° C. In some embodiments, the reaction temperature is about 50° C. to about 55° C.

In some embodiments, the catalytic hydrogenation employs a metal catalyst. In some embodiments, the metal catalyst comprises nickel. In some embodiments, the metal catalyst comprises Raney nickel. The amount of catalyst used can vary depending on the catalyst and other reaction conditions selected. In some embodiments, the amount of Raney nickel used is (expressed as a mol % based on the amount of compound of Formula II) at least about 1 mol %, at least about 5 mol %, at least about 10 mol %, at least about 15 mol %, at least about 20 mol %, at least about 25 mol %, at least about 30 mol %, at least about 35 mol %, at least about 40 mol %, at least about 45 mol %, at least about 50 mol %, or at least about 60 mol %.

The amount of hydrogen used (expressed as kg pressure per $cm^3$ of catalyst) will also vary depending on the amount of catalyst and other reaction conditions selected. In some embodiments, the amount of hydrogen is at least about 1 $kg/cm^3$, at least about 2 $kg/cm^3$, at least about 3 $kg/cm^3$, at least about 4 $kg/cm^3$, at least about 5 $kg/cm^3$, at least about 6 $kg/cm^3$, at least about 7 $kg/cm^3$, at least about 8 $kg/cm^3$, at least about 9 $kg/cm^3$, at least about 10 $kg/cm^3$, at least about 11 $kg/cm^3$, at least about 12 $kg/cm^3$, at least about 15 $kg/cm^3$, at least about 20 $kg/cm^3$, or at least about 25 $kg/cm^3$. In some embodiments, the reaction employs about 20 mol % Raney nickel and about 10 $kg/cm^3$ $H_2$.

The reaction time is in general the length of time required for the reaction to go substantially to completion, which may vary with the particular conditions and reaction temperature selected. In some embodiments, the reaction time is at least about 30 minutes, at least about 1 hour, at least about 4 hours, at least about 8 hours, at least about 10 hours, at least about 12 hours, at least about 16 hours, at least about 20 hours, or at least about 24 hours. In some embodiments, the reaction time is less than about 48 hours, less than about 40 hours, less than about 36 hours, less than about 30 hours, less than about 24 hours, less than about 18 hours, or less than about 14 hours. In some embodiments, the reaction time is about 12 hours.

(B) The crude compound of Formula I reaction mixture is (i) filtered, (ii) the residue washed with a first solvent, then (iii) concentrated to about 10-20% of the reaction mixture volume, and (iv) the reaction mixture subjected to a second solvent in which the compound is less soluble, (v) filtered and (vi) dried to provide a semi-purified product.

The first solvent (step ii) may be a lower alkyl alcohol, dimethylsulfoxide (DMSO), or dimethylformamide (DMF). In some embodiments, the first solvent is methanol or ethanol. In some embodiments, the second solvent (step iv) is ethyl acetate. The filtering process (steps i and v) may comprise suction filtering, and further comprise washing the solid with additional second solvent.

In some embodiments, the drying process (step vi) may include suction drying, drying under reduced pressure, drying at an elevated temperature, or a combination thereof. In some embodiments, the drying process includes suction drying, followed by drying under reduced pressure at a temperature of at least 35° C. In some embodiments, the reduced pressure is less than 600 mmHg, less than 500 mmHg, less than 400 mmHg, less than 300 mmHg, or less than 200 mmHg.

In some embodiments, the drying temperature is at least about 40° C., at least about 45° C., or at least about 50° C. The drying temperature is less than the melting point of the compound of Formula I, and less than the decomposition temperature of the compound of Formula I. In some embodiments, the drying temperature is less than about 120° C., less than about 110° C., less than about 100° C., less than about 90° C., less than about 80° C., less than about 70° C., or less than about 65° C.

(C) The semi-purified product at this point may still contain an unacceptable amount of nickel (or other catalyst metal). To further purify the product, the dried solid is (i) subjected to water, (ii) heated at an elevated temperature and stirred to form a slurry, (iii) cooled and (iv) filtered, (v) dried a first time, (vi) taken up in a mixture of ethanol and acetic acid, (vii) heated to a holding temperature, (viii) cooled, (ix) filtered and (x) dried a second time to provide a nickel-depleted product. In some embodiments, the elevated temperature of step ii is at least about 30° C., at least about 35° C., at least about 40° C., at least about 45° C., at least about 50° C., at least about 55° C., at least about 60° C., or at least about 65° C. In some embodiments, the elevated temperature is less than about 100° C., less than about 90° C., less than about 80° C., less than about 70° C., or less than about 65° C. In some embodiments, the elevated temperature is about 55° C.

In some embodiments, the filtering process of step iv includes suction filtering and washing with water. In some embodiments, the drying step of step v includes suction drying followed by drying under reduced pressure at a temperature of at least 35° C. In some embodiments, the reduced pressure is less than 600 mmHg, less than 500 mmHg, less than 400 mmHg, less than 300 mmHg, or less than 200 mmHg.

In some embodiments, the drying temperature of step v is at least about 40° C., at least about 45° C., or at least about 50° C. The drying temperature is less than the melting point of the compound of Formula I, and less than the decomposition temperature of the compound of Formula I. In some embodiments, the drying temperature is less than about 120° C., less than about 110° C., less than about 100° C., less than about 90° C., less than about 80° C., less than about 70° C., or less than about 65° C. In some embodiments, the drying temperature of step v is about 45° C.

In step vi, the ratio of ethanol to acetic acid may range from about 1:20 to about 20:1. In some embodiments, the ratio is about 1:1, about 2:1, about 3:1, about 4:1, about 5:1, about 6:1, about 7:1, about 8:1, about 9:1, or about 10:1, v/v ethanol:acetic acid. In some embodiments, the holding temperature of step vii is at least about 30° C., at least about 35° C., at least about 40° C., at least about 45° C., at least about 50° C., at least about 55° C., at least about 60° C., or at least about 65° C. In some embodiments, the holding temperature is about the reflux temperature of the solvent mixture of ethanol and acetic acid, or less than about 80° C., less than about 75° C., less than about 70° C., less than about 65° C., or less than about 60° C. In some embodiments, the holding temperature is about the reflux temperature of the solvent mixture.

In some embodiments, the mixture is maintained at the holding temperature for a time period of at least about 10 minutes, at least about 20 minutes, at least about 30 minutes, at least about 45 minutes, at least about 60 minutes, at least about 90 minutes, at least about 120 minutes, at least about 150 minutes, at least about 240 minutes, or at least about 3 hours. In some embodiments, the time period is no more than about 5 hours, no more than about 4 hours, no more than about 3 hours, no more than about 2 hours, no more than about 1 hour, or no more than about 30 minutes. In some embodiments, the time period is about 1 hour.

The cooling of step viii is performed over a time period of at least about 10 minutes, at least about 20 minutes, at least about 30 minutes, at least about 45 minutes, at least about 1 hour, or at least about 2 hours. The final temperature of step viii is less than about 35° C., less than about 30° C., less than about 25° C., less than about 20° C., less than about 15° C., less than about 10° C., or less than about 5° C. In some embodiments, the final temperature of step viii is about ambient temperature.

In some embodiments, step viii further comprises stirring the mixture. The filtering of step ix may further include washing with a lower alkyl alcohol. In some embodiments, the filtered solids are washed with ethanol. The drying step of step x may include suction drying, drying under reduced pressure, drying at an elevated temperature, or a combination thereof.

In some embodiments, the drying process of step x includes suction drying followed by drying under reduced pressure at a temperature of at least 35° C. In some embodiments, the reduced pressure is less than 600 mmHg, less than 500 mmHg, less than 400 mmHg, less than 300 mmHg, or less than 200 mmHg. In some embodiments, the drying temperature of step x is at least about 40° C., at least about 45° C., or at least about 50° C. The drying temperature is less than the melting point of the compound of Formula I, and less than the decomposition temperature of the compound of Formula I. In some embodiments, the drying temperature is less than about 120° C., less than about 110° C., less than about 100° C., less than about 90° C., less than about 80° C., less than about 70° C., or less than about 65° C. In some embodiments, the drying temperature of step x is about 45° C.

In some embodiments, steps vi-x are repeated 1, 2, or 3 times. In some embodiments, steps vi-x are repeated once.

D. Process 4:

(A) The nickel-depleted product of Process 3 is further purified by (i) contacting the compound with a first solvent, (ii) raising the mixture to a first elevated temperature, (iii) adding a second solvent, (iv) cooling the resulting mixture to a crystallizing temperature, (v) stirring the mixture, (vi) filtering the solid, and (vii) drying the solid, to provide a compound of Formula I as a pure anhydrous crystalline form. In some embodiments, the first solvent of step (i) is methanol, ethanol, 1-propanol, or 2-propanol, or a mixture thereof. In some embodiments, the lower alkyl alcohol is methanol.

The first elevated temperature of step (ii) is at least about 30° C., at least about 35° C., at least about 40° C., at least about 45° C., at least about 50° C., at least about 55° C., at least about 60° C., or at least about 65° C. The elevated temperature will be no greater than the reflux temperature of the first solvent, or no more than about 80° C., no more than about 75° C., no more than about 70° C., no more than about 60° C., no more than about 55° C., no more than about 50° C., no more than about 45° C., no more than about 40° C., or no more than about 35° C. In some embodiments, the elevated temperature is about 55° C.

In some embodiments, step ii further comprises maintaining the mixture at or near the elevated temperature until the compound of Formula I has completely dissolved, and a clear solution has formed. In some embodiments, step ii further includes slowly cooling the solution to a second elevated temperature. In some embodiments, the second elevated temperature is about 5° C., about 10° C., about 15° C., or about 20° C. lower than the first elevated temperature. The second elevated temperature is about 5° C., about 10° C., about 15° C., about 20° C., or above 20° C.

In some embodiments, step ii also includes filtering the solution.

The second solvent of step iii is MTBE or THF. In some embodiments, the second solvent is MTBE. In some embodiments, the first solvent and second solvent are anhydrous. In some embodiments, the second solvent is added slowly, over an extended time period. In some embodiments, the extended time period of step ii is at least about 20 minutes, at least about 30 minutes, at least about 45 minutes, at least about 60 minutes, at least about 75 minutes, at least about 90 minutes, at least about 105 minutes, at least about 120 minutes, at least about 150 minutes, at least about 180 minutes, or at least about 240 minutes. The extended time period is less than about 24 hours, less than about 18 hours, less than about 12 hours, less than about 8 hours, less than about 6 hours, less than about 5 hours, less than about 4 hours, less than about 3 hours, less than about 2 hours, or less than about 1 hour. In some embodiments, the extended time period is about 2 hours.

In some embodiments, step iii further includes adding a seed crystal. The ratio of the first solvent to the second solvent can vary from about 1:20 to about 20:1, v/v. In some embodiments, the ratio of MeOH to MTBE is about 5:1, about 4:1, about 3:1, about 2.7:1, about 2.5:1, about 2.3:1, about 2:1, about 1.5:1, about 1.3:1, about 1.2:1, about 1:1, about 1:1.5, about 1:2, about 1:3, or about 1:4.

The crystallizing temperature of step iv is no more than about 35° C., less than about 30° C., less than about 25° C., less than about 20° C., less than about 15° C., less than about 10° C., or less than about 5° C. In some embodiments, the crystallizing temperature is about 25° C. The cooling occurs over an extended time period. In some embodiments, the cooling time of step iv is at least about 20 minutes, at least about 30 minutes, at least about 45 minutes, at least about 60 minutes, at least about 75 minutes, at least about 90 minutes, at least about 105 minutes, at least about 120 minutes, at least about 150 minutes, or at least about 180 minutes. In some embodiments, the cooling time is about 45 minutes to about 90 minutes.

In some embodiments, step v further includes adding an additional amount of the second solvent over an extended period of time. In some embodiments, the extended time period of step v is at least about 20 minutes, at least about 30 minutes, at least about 45 minutes, at least about 60 minutes, at least about 75 minutes, at least about 90 minutes, at least about 105 minutes, at least about 120 minutes, or at least about 150 minutes. The extended time period is less than about 24 hours, less than about 18 hours, less than about 12 hours, less than about 8 hours, less than about 6 hours, less than about 5 hours, less than about 4 hours, less than about 3 hours, less than about 2 hours, or less than about 1 hour.

The filtering step of step vi can further include washing the solid with an additional amount of the second solvent. The drying step of step vii may include suction drying, drying under reduced pressure, drying at an elevated temperature, or a combination thereof. In some embodiments, the drying process of step x includes suction drying followed by drying under reduced pressure at a temperature of at least 35° C. In some embodiments, the reduced pressure is less than 600 mmHg, less than 500 mmHg, less than 400 mmHg, less than 300 mmHg, or less than 200 mmHg. In some embodiments, the drying temperature of step vii is at least about 40° C., at least about 45° C., or at least about 50° C. The drying temperature is less than the melting point of the compound of Formula I, and less than the decomposition temperature of the compound of Formula I. In some embodiments, the drying temperature is less than about 120° C., less than about 110° C., less than about 100° C., less than about 90° C., less than about 80° C., less than about 70° C., or less than about 65° C. In some embodiments, the drying temperature of step vii is about 45° C.

Intermediates Useful in the Processes

Compounds of Formula II and Formula III are useful for preparing the compounds of Formula I:

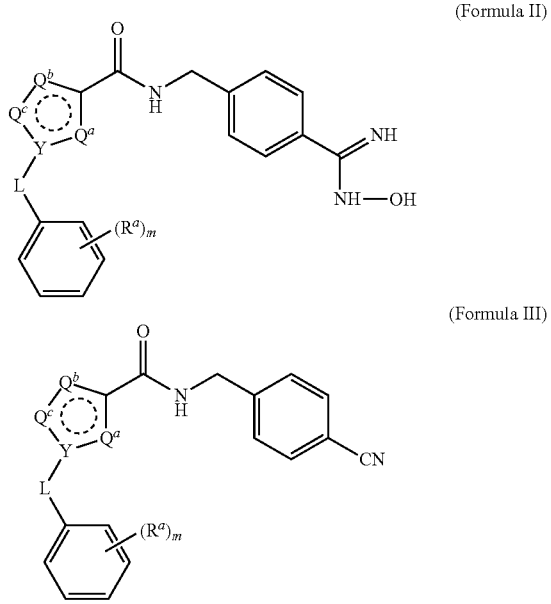

where the substituents are as described above.

Formulations

The compounds of Formula I are formulated and administered according to methods known in the art. The pharmaceutical compositions containing the active ingredient may be in a form suitable for oral use, for example, as tablets, troches, lozenges, aqueous or oily suspensions, dispersible powders or granules, emulsions and self-emulsifications as described in US 2002-0012680, hard or soft capsules, syrups, elixirs, solutions, buccal patch, oral gel, chewing gum, chewable tablets, effervescent powder and effervescent tablets.

Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application includes the use of mouth washes and gargles.

The compounds of Formula I may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

The inhibitory agent of Formula I may be deposited within a medical device, such as a stent, and delivered to the treatment site for treatment of a portion of the body. Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), and U.S. Pat. No. 4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz) and in WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example.

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinyl-pyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethylcellulose.

Polymers and semipermeable polymer matrices may be formed into shaped articles, such as valves, stents, tubing, prostheses and the like. Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

The compound of Formula I can be formulated for release from the polymer coating into the environment in which the medical device is placed. For example, the compound is released in a controlled manner over an extended time frame (e.g., months) using at least one of several well-known techniques involving polymer carriers or layers to control elution. Some of these techniques were previously described in US 2004/0243225, the entire disclosure of which is incorporated in its entirety.

Moreover, as described for example in U.S. Pat. No. 6,770,729, which is incorporated herein in its entirety, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Some embodiments of the invention include a device having a plurality of polymer coatings, each having a plurality of diffusion coefficients. In some embodiments, the release of the inhibitory agent from the polymer coating can be modulated by the plurality of polymer coatings.

The release of the inhibitory agent from the polymer coating can be controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

EMBODIMENTS

One aspect of the invention is a process for preparing a compound of Formula I, or a salt thereof.

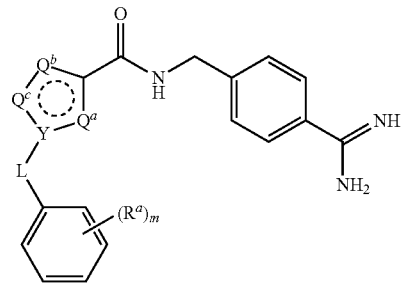

(Formula I)

wherein the subscript m is an integer of from 0 to 3; each $R^a$ is independently selected from the group consisting of $(C_3-C_8)$cycloalkyl, $(C_1-C_4)$haloalkyl, halogen, —OH, —OR$^1$, —SH, —SR$^1$, —S(O)R$^1$, —S(O)$_2$R$^1$, —SO$_2$NH$_2$, —C(O)NH$_2$, —C(O)NHR$^1$, —C(O)N(R$^1$)$_2$, —C(O)R$^1$, —C(O)H, —CO$_2$H, —CO$_2$R$^1$, —NO$_2$, —NH$_2$, —NHR$^1$, —N(R$^1$)$_2$, wherein each R$^1$ is independently $(C_1-C_8)$alkyl; L is a linking group selected from the group consisting of a bond or CH$_2$; Q$^a$, Q$^b$, and Q$^c$ are each members independently selected from the group consisting of N, S, O and C(R$^q$) wherein each R$^q$ is independently selected from the group consisting of H, C$_{1-8}$ alkyl, halo and phenyl, and the ring having Q$^a$, Q$^b$, Q$^c$ and Y as ring vertices is a five-membered ring having two double bonds; and Y is selected from the group consisting of C and N; the method comprising subjecting a compound of Formula II to reducing conditions, to provide the compound of Formula I as a crude product

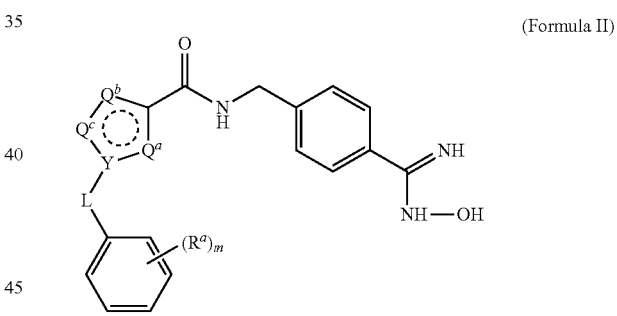

(Formula II)

In some embodiments, the reducing conditions comprise Raney nickel and H$_2$. In some embodiments, the reducing conditions comprise Raney nickel at about 10 to about 40 mol %, and H$_2$ at about 2 to about 20 kg/cm$^3$. In some embodiments, the reducing conditions comprise Raney nickel at about 20 mol %, and H$_2$ at about 10 kg/cm$^3$.

In some embodiments, the reducing conditions further comprise using acetic acid as a solvent, and heating at a temperature of about 30° C. to about 70° C. In some embodiments, the temperature is about 50° C. to about 65° C.

In some embodiments, the heating is performed for about 15 minutes to 2 hours. In some embodiments, the heating is performed for about 15 minutes to 1 hour. In some embodiments, the heating is performed the heating is performed for about 30 minutes.

In some embodiments, the process further comprises forming a slurry of the crude product in water at a temperature of about 25° C. to about 70° C. to provide a nickel-depleted product. In some embodiments, the temperature is about 50° C. to about 60° C. In some embodiments, the slurry is stirred for about one hour.

In some embodiments, the process further comprises heating the nickel-depleted product in a solvent to remove further nickel. In some embodiments, the solvent comprises a mixture of ethanol and acetic acid. In some embodiments, the solvent comprises a mixture of methanol, dimethyl glyoxime, and methyl-t-butyl ether.

In some embodiments, the compound of Formula II is obtained by subjecting a compound of Formula III to hydroxylamine or a salt thereof under basic conditions.

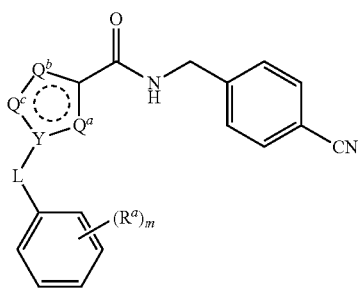

(Formula III)

In some embodiments, the basic conditions comprise triethylamine and ethanol. In some embodiments, the basic conditions further comprise heating at a temperature of about 50° C. to about 75° C. In some embodiments, the basic conditions comprise heating at a temperature of about 60° C. to about 65° C. In some embodiments, the heating is performed for about 3 hours to about 12 hours. In some embodiments, the heating is performed for about 7 hours. In some embodiments, about 3 equivalents of hydroxylamine and triethylamine are used per equivalent of compound of Formula III.

In some embodiments of the invention, the compound of Formula III is obtained by subjecting a compound of Formula IV to 4-(aminomethyl)benzonitrile hydrochloride under aprotic conditions.

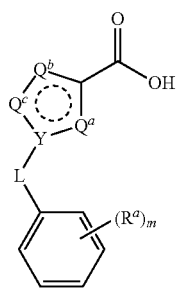

(Formula IV)

In some embodiments, the aprotic conditions comprise triethylamine in dichloromethane. In some embodiments, the aprotic conditions further comprise 1-propanephosphonic anhydride in ethyl acetate (T3P®). In some embodiments, the aprotic conditions comprise incubating the compound of Formula IV with 4-(aminomethyl)benzonitrile hydrochloride and 1-propanephosphonic anhydride at a temperature of about 5° C. to about 39° C. In some embodiments, the temperature is about 20° C. to about 30° C. In some embodiments, the aprotic condition further comprises stirring for 1 to 6 hours In some embodiments, the aprotic condition further comprises stirring for 3 hours.

In some embodiments, the compound of Formula I is selected from the group consisting of:

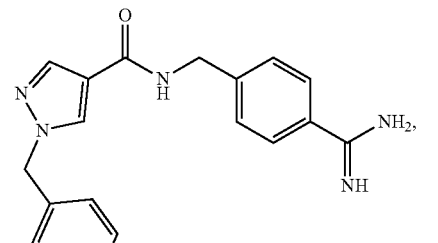

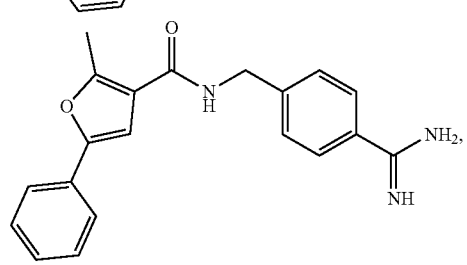

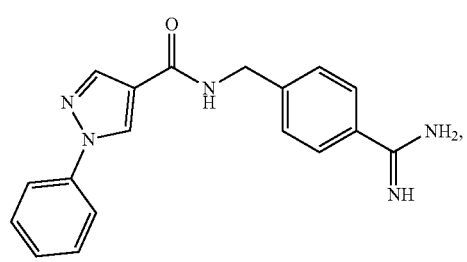

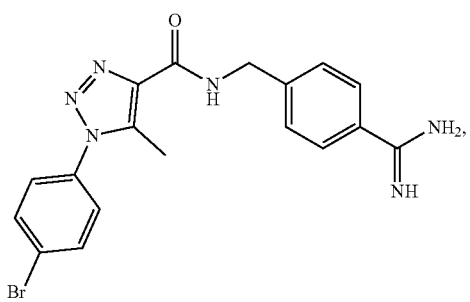

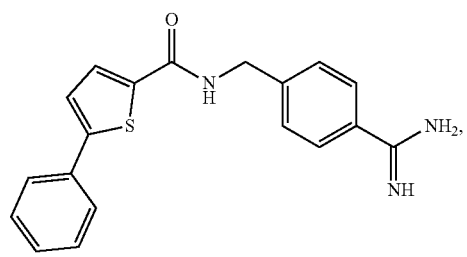

-continued

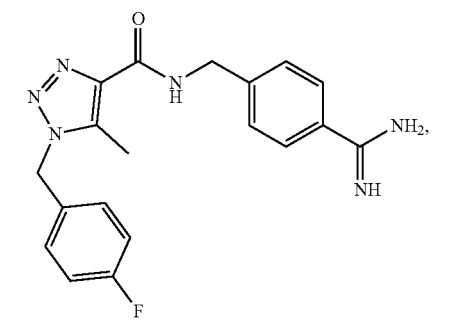
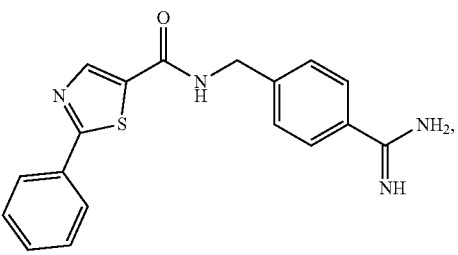
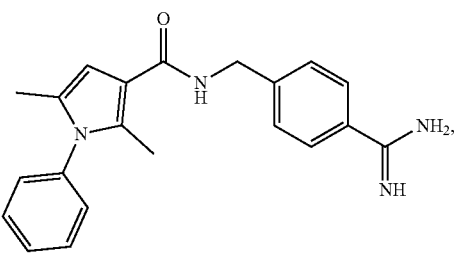
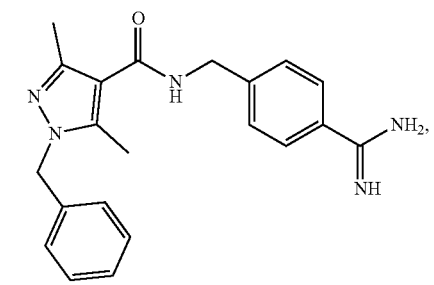
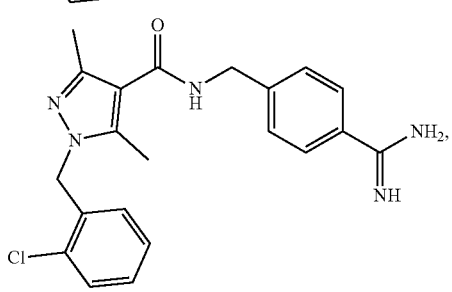
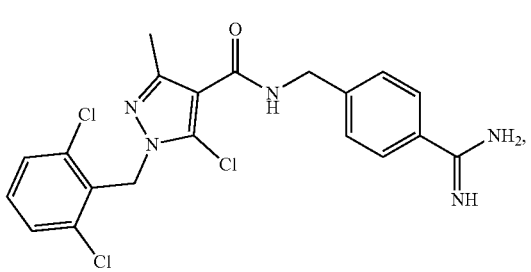

-continued

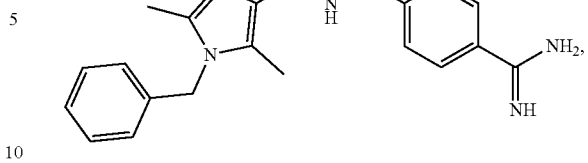
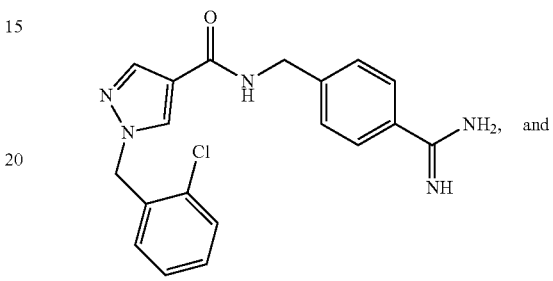
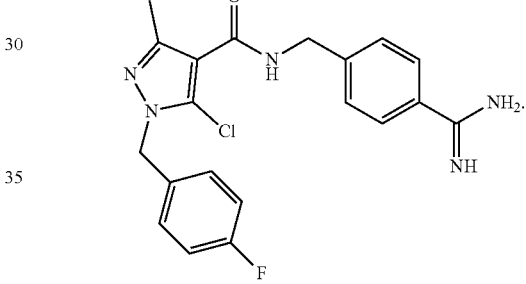

In some embodiments, the compound of Formula I is 1-benzyl-N-(4-carbamimidoyl-benzyl)-1H-pyrazole-4-carboxamide or a salt thereof. In some embodiments, the compound of Formula I is 1-benzyl-N-(4-carbamimidoyl-benzyl)-1H-pyrazole-4-carboxamide acetate.

EXAMPLES

The following examples are provided as illustration, and are not intended to limit the claimed invention. In the examples below, concentration under reduced pressure is performed at 500-600 mmHg unless otherwise specified. The following abbreviations are used: DCM=dichloromethane; MeOH=methanol; EtOH=ethanol; AcOH=acetic acid; EtOAc and AcOEt=ethyl acetate; T3P®=50% 1-propanephosphonic anhydride in EtOAc; MTBE=methyl t-butyl ether.

Example 1: Synthesis of Compounds of Formula IV

Compounds of Formula IV are purchased from commercial sources, or are prepared by the methods described below, or other methods known in the art.

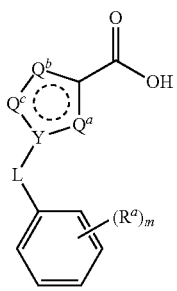

(Formula IV)

wherein the subscript m is an integer of from 0 to 3; each $R^a$ is independently selected from the group consisting of $(C_3-C_8)$cycloalkyl, $(C_1-C_4)$-haloalkyl, halogen, —OH, —$OR^1$, —SH, —$SR^1$, —$S(O)R^1$, —$S(O)_2R^1$, —$SO_2NH_2$, —$C(O)NH_2$, —$C(O)NHR^1$, —$C(O)N(R^1)_2$, —$C(O)R^1$, —C(O)H, —$CO_2H$, —$CO_2R^1$, —$NO_2$, —$NH_2$, —$NHR^1$, —$N(R^1)_2$, wherein each $R^1$ is independently $(C_1-C_8)$alkyl; L is a linking group selected from the group consisting of a bond or $CH_2$; $Q^a$, $Q^b$, and $Q^c$ are each members independently selected from the group consisting of N, S, O and $C(R^q)$ wherein each $R^q$ is independently selected from the group consisting of H, $C_{(1-8)}$alkyl, halo and phenyl, and the ring having $Q^a$, $Q^b$, $Q^c$ and Y as ring vertices is a five-membered ring having two double bonds; and
Y is selected from the group consisting of C and N.

Ethyl 1H-pyrazole-4-carboxylate (23.5 g, 1 eq) and acetone (587 mL) was charged into a round bottom flask under $N_2$ atmosphere at 20-25° C., and the mixture was stirred for 10 minutes, followed by the addition of $K_2CO_3$ (70.4 g, 3 eq). the reaction mass was cooled to 0-5° C., and benzyl bromide (28.66 g, 1.1 eq) was added very slowly at 0-5° C. over a period of 15 minutes. The reaction mixture was raised to 20-25° C., then heated to 50-60° C. and maintained at that temperature for 3 hours. After the reaction was complete (monitored by HPLC), the reaction mixture was concentrated under reduced pressure at 45-50° C., quenched with 10% NaOH, and extracted with DCM (117 mL). The aqueous layer was separated, back extracted with DCM (117 mL), and the combined organic layers dried over sodium sulfate and concentrated under reduced pressure at 45-50° C. Petroleum ether or n-heptane (117 mL) was added to the concentrate and stirred for 1 hour, then filtered and dried under reduced pressure at 40-45° C. for 12 hours to yield ethyl 1-benzyl-1H-pyrazole-4-carboxylate (32.5 g).

Ethyl 1-benzyl-1H-pyrazole-4-carboxylate (30 g) and methanol (300 mL) were charged into a 3 L round bottom flask, and the resulting solution stirred for 10 minutes at 24° C. KOH (14.6 g, 2 eq) was then added, and the mixture heated to 65-70° C. and maintained for 4 hours. After the reaction was completed (as determined by HPLC), the reaction mixture was concentrated at 45-50° C. under reduced pressure to 40-60 mL. The resulting residue was dissolved in water (300 mL) and extracted with DCM (2×150 mL). The aqueous layer was separated and acidified with 6 N HCl to a pH of 2. The precipitated solids were filtered, washed with water (30 mL), and dried at 45-50° C. under reduced pressure for 12 hours to provide 1-benzyl-1H-pyrazole-4-carboxylic acid (19.5 g) as a pale brown solid, purity 99.1% by HPLC. $^1$H NMR (400 MHz, DMSO-d6): δ 5.36 (s, 2H), 7.26-7.37 (m, 5H), 7.83 (s, 1H), 8.38 (s, 1H), 12.33 (broad S, 1H).

Other compounds of Formula IV are prepared by similar methods, varying the benzyl and pyrazole components as needed.

Example 2: Synthesis of Compounds of Formula III

Compounds of Formula III, where the substituents are as described in Example 1 above, are prepared as described below:

Formula III

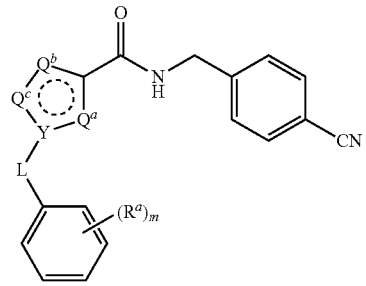

DCM (285 mL) and 4-aminomethyl-benzonitrile hydrochloride (19.2 g, 1.2 eq) were charged into a 3 L round bottom flask, and the mixture cooled to 0° C. Triethylamine (39.4 g, 3 eq) was added at 0° C., and the resulting mixture was stirred for 30 minutes. Next, 1-benzyl-1H-pyrazole-4-carboxylic acid (19 g, 1 eq) was added at 0-5° C., and the temperature raised to 20-25° C. 1-Propanephosphonic anhydride in 50% ethyl acetate (T3P®, Spectrochem, 72 mL, 1.28 eq) was added and stirred at 20-25° C. for 3 hours. After the reaction completed, water (95 mL) was added and stirred for 10-15 minutes, and the organic layer separated. The aqueous layer was extracted again with DCM (95 mL), and the organic layers combined and washed with water (95 mL). The organic layer was dried over $Na_2SO_4$ and concentrated under reduced pressure to about 40 mL. Acetone (95 mL) was then added, and the mixture was co-distilled until only 20-30 mL remained in the pot. Water (285 mL) was then added and stirred for 1 hour at 20-25° C. The resulting solids were filtered and washed with acetone:water (1:3 v/v, 10 mL), then suction filtered and dried under reduced pressure at 45-50° C. for 12 hours to yield 1-benzyl-N-(4-cyano-benzyl)-1H-pyrazole-4-carboxamide (26.9 g, 94%) as a light brown solid, 98.51% pure by HPLC. $^1$H NMR (400 MHz, DMSO-d6): δ 4.49 (d, J=5.9 Hz, 2H), 5.37 (s, 2H), 7.27-7.38 (m, 5H), 7.48 (d, J=8.1 Hz, 2H), 7.79 (d, J=8.1 Hz, 2H), 7.95 (s, 1H), 8.31 (s, 1H), 8.77 (t, J=5.9 Hz, 1H).

Other compounds of Formula III are prepared by the same method, using the other compounds prepared in Example 1.

Example 3: Synthesis of Compounds of Formula II

Compounds of Formula II, where the substituents are as described in Example 1 above, are prepared as described below:

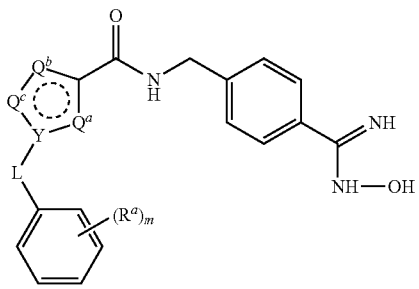

Formula II

Ethanol (250 mL) and 1-benzyl-N-(4-cyanobenzyl)-1H-pyrazole-4-carboxamide (25 g) were charged in a 1 L round bottom flask under nitrogen atmosphere at 20-25° C. Hydroxylamine hydrochloride (16.3 g, 3 eq) and triethylamine (24.64 g, 3 eq) were added to the reaction mixture at 20-25° C. The mixture was then heated to 60-65° C., and maintained at that temperature for 7 hours. After the reaction was complete, the mixture was concentrated to about 30-50 mL under reduced pressure at 45-50° C. Water (250 mL) was then added and stirred at ambient temperature for 30 minutes. The resulting solids were filtered, washed with water (125 mL), and suction filtered to dryness, then suction dried further under reduced pressure at 45-50° C. for 12 hours to yield 1-benzyl-N-(4-(N-hydroxycarbamimidoyl)benzyl)-1H-pyrazole-4-carboxamide (25.5 g, 92.3 yield) as a pale yellow solid, 95.41% pure by HPLC. $^1$H NMR (400 MHz, DMSO-d6): δ 4.40 (d, J=5.9 Hz, 2H), 5.34 (s, 2H), 5.76 (broad s, 2H), 7.25-7.37 (m, 7H), 7.61 (d, J=8.2 Hz, 2H), 7.91 (s, 1H), 8.27 (s, 1H), 8.63 (t, J=5.9 Hz, 1H), 9.57 (broad s, 1H).

Other compounds of Formula II are prepared by the same method, using the other compounds prepared in Example 2.

Example 4: Synthesis of Compounds of Formula I

Compounds of Formula I, where the substituents are as described in Example 1 above, are prepared as described below:

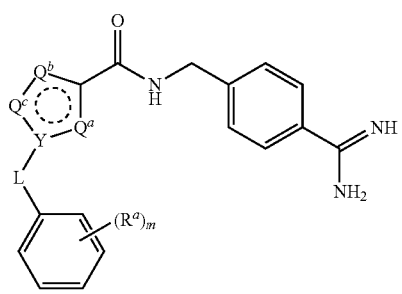

Formula I

Acetic acid (2100 g) and 1-benzyl-N-(4-(N-hydroxycarbamimidoyl)benzyl)-1H-pyrazole-4-carboxamide (200 g) were stirred at 25° C. for 10-15 minutes in a hydrogenator.

Raney nickel (40 g) and water (1 volume) were slurried in a flask, then allowed to settle for 5 minutes. The water was decanted, and another volume of water added, slurried, allowed to settle for 5 minutes, and decanted. Acetic acid (1 volume) was added, the mixture slurried for 10 minutes, then allowed to settle for 5 minutes and decanted. The Raney nickel together with acetic acid (1 volume) were then charged into the hydrogenator. The reaction mixture was heated to 60° C., and hydrogen applied (10 Kg pressure) for 30 minutes.

The resulting mixture was allowed to cool to ambient temperature, and the resulting solids suction filtered for 30 minutes on Celite®. The solids were washed with MeOH (784 g), concentrated to 1-2 volumes, and charged with EtOAc (2 L). The mixture was stirred for 1 hour at 25° C., then suction filtered, washed with EtOAc (400 g), and suction dried for 2 hours. The product was further dried under reduced pressure (<300 mmHg) at 25° C. for 2 hours at 25° C., followed by drying under reduced pressure (<300 mmHg) at 45° C. for 12 hours to yield 1-benzyl-N-(4-carbamimidoylbenzyl)-1H-pyrazole-4-carboxamide acetate (220 g) as a crude product.

Other compounds of Formula I are prepared by the same method, using the compounds prepared in Example 3.

Example 5: Purification

The dried product (219 g) was cooled to 25° C., and charged into a round bottom flask with water (2190 mL) and stirred for 10 minutes to form a slurry. The slurry was heated to 55° C. over 20 minutes, stirred for an hour at that temperature, cooled to 25° C. over 20 minutes with stirring, and stirred for an additional 30 minutes at 25° C. The solids were filtered, washed with water (220 mL), and suction dried for 2 hours. The product was dried again under reduced pressure (<300 mmHg) at 45° C. for 12 hours, then cooled to 25° C. and charged into a round bottom flask. To this was added absolute ethanol (1250 g) and acetic acid (183 g), and the mixture heated to reflux temperature (75° C.) over 30 minutes, and maintained at reflux for 30 minutes. The mixture was then slowly cooled to 25° C. over 30 minutes, stirred at 25° C. for 45 minutes, filtered and washed with EtOH, then suction dried for 2 hours at 25° C. The product was then dried under reduced pressure (<300 mmHg) at 45° C. for 10 hours.

The dried product (143 g) was cooled to 25° C., and charged into a round bottom flask with absolute ethanol (1027 g) and acetic acid (150 g), and the mixture heated to reflux temperature (75° C.) over 30 minutes, and maintained at reflux for 1 hour. The mixture was then slowly cooled to 25° C. over 45 minutes, stirred at 25° C. for 45 minutes, filtered and washed with EtOH, then suction dried for 2 hours at 25° C. The product was then dried under reduced pressure (<300 mmHg) at 45° C. for 12 hours to provide purified 1-benzyl-N-(4-carbamimidoylbenzyl)-1H-pyrazole-4-carboxamide acetate (126 g, 56% yield, 99.6% pure by HPLC), having less than 30 ppm nickel.

Example 6: Pure Crystalline Form

A mixture of crude 1-benzyl-N-(4-carbamimidoylbenzyl)-1H-pyrazole-4-carboxamide acetate (10 g) in MeOH (450 mL) was charged into a 2 L round bottom flask, and the mixture heated to 50-55° C. to obtain a clear solution. The solution was maintained at 50-55° C. for 30 minutes, filtered, and charged to a reactor at 50-55° C. MTBE (450 mL) was slowly added at 50-55° C., and the mixture cooled to 25° C. over 1 hour. A white suspension was observed with cooling. MTBE (450 mL) was added slowly at 20-25° C., and the resulting mixture was stirred for 16 hours, filtered, and washed with MTBE (10 mL). The product was dried under reduced pressure at 50-55° C. for 24 hours to provide pure 1-benzyl-N-(4-carbamimidoylbenzyl)-1H-pyrazole-4-carboxamide acetate (8.25 g, 82.5% yield) in the anhydrous crystalline polymorphic form ("Form 1") as an off-white solid. The product purity was >99% by HPLC, and contained less than 14.5 ppm nickel. $^1$H NMR (300 MHz, DMSO-d6): δ 1.71 (s, 3H), 4.47 (d, J=5.4 Hz, 2H), 5.36 (s, 2H), 7.26-7.37 (m, 5H), 7.46 (d, J=7.8 Hz, 2H), 7.74 (d, J=7.8 Hz, 2H), 7.92 (s, 1H), 8.29 (s, 1H), 8.77 (broad s, 1H), 10.34 (broad s, 3 H). $^{13}$C NMR (75 MHz, DMSO-d6): δ 24.7, 41.7, 55.0, 118.4, 127.4 (2C), 127.5 (2C), 127.8 (2C), 128.2 (2C), 128.6 (2C), 131.6, 136.8, 145.2, 161.8, 165.7, 176.5.

What is claimed is:

1. A process for preparing a compound of Formula I

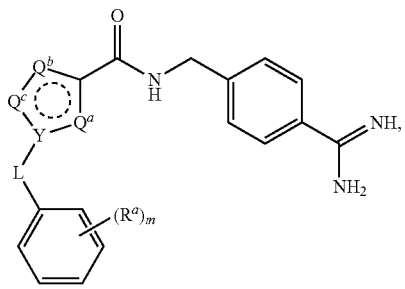

(Formula I)

or a salt thereof,
wherein the subscript m is an integer of from 0 to 3;
each $R^a$ is independently selected from the group consisting of $(C_3-C_8)$cycloalkyl, $(C_1-C_4)$haloalkyl, halogen, —OH, —OR$^1$, —SH, —SR$^1$, —S(O)R$^1$, —S(O)$_2$R$^1$, —SO$_2$NH$_2$, —C(O)NH$_2$, —C(O)NHR$^1$, —C(O)N(R$^1$)$_2$, —C(O)R$^1$, —C(O)H, —CO$_2$H, —CO$_2$R$^1$, —NO$_2$, —NH$_2$, —NHR$^1$, —N(R$^1$)$_2$, wherein each R$^1$ is independently $(C_1-C_8)$alkyl;
L is a linking group selected from the group consisting of a bond or CH$_2$;
$Q^a$, $Q^b$, and $Q^c$ are each members independently selected from the group consisting of N, S, O and $C(R^q)$ wherein each $R^q$ is independently selected from the group consisting of H, $C_{1-8}$ alkyl, halo and phenyl, and the ring having $Q^a$, $Q^b$, $Q^c$ and Y as ring vertices is a five-membered ring having two double bonds; and
Y is selected from the group consisting of C and N;
the method comprising:
(a) subjecting a compound of Formula II to reducing conditions, to provide the compound of Formula I as a crude product, wherein the compound of Formula II is:

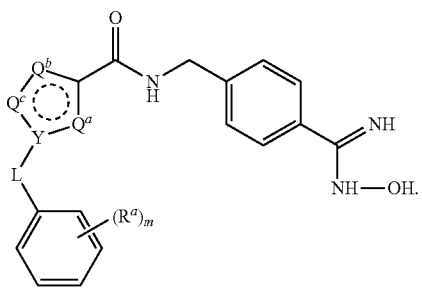

(Formula II)

2. The process of claim 1, wherein the reducing conditions comprise Raney nickel and H$_2$.

3. The process of claim 2, wherein the reducing conditions comprise Raney nickel at about 10 to about 40 mol %, and H$_2$ at about 2 to about 20 kg/cm$^3$.

4. The process of claim 3, wherein the reducing conditions comprise Raney nickel at about 20 mol %, and H$_2$ at about 10 kg/cm$^3$.

5. The process of claim 1, wherein the reducing conditions further comprise acetic acid as a solvent, and heating at a temperature of about 30° C. to about 70° C.

6. The process of claim 2, further comprising:
(b) forming a slurry of the crude product in water at a temperature of about 25° C. to about 70° C. to provide a nickel-depleted product.

7. The process of claim 6, further comprising:
(c) heating the nickel-depleted product in a solvent to remove further nickel.

8. The process of claim 7, wherein the solvent comprises a mixture of ethanol and acetic acid.

9. The process of claim 7, wherein the solvent comprises a mixture of methanol, dimethyl glyoxime, and methyl-t-butyl ether.

10. The process of claim 1, wherein the compound of Formula II is obtained by combining a compound of Formula III with hydroxylamine or a salt thereof under basic conditions, wherein the compound of Formula III is:

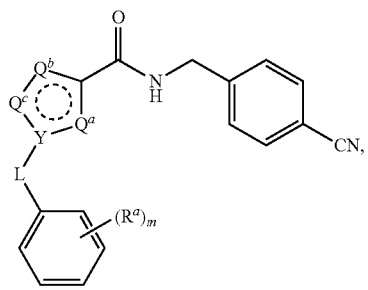

(Formula III)

to provide the compound of Formula II.

11. The process of claim 10, wherein the basic conditions comprise triethylamine and ethanol.

12. The process of claim 11, wherein the basic conditions further comprise heating at a temperature of about 50° C. to about 75° C.

13. The process of claim 10, wherein about 3 equivalents of hydroxylamine and triethylamine are used per equivalent of compound of Formula III.

14. The process of claim 10, wherein the compound of Formula III is obtained by reacting a compound of Formula IV with 4-(aminomethyl)benzonitrile hydrochloride under aprotic conditions, wherein the compound of Formula IV is:

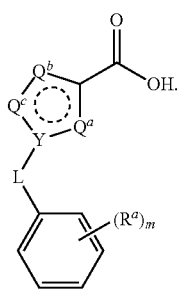

(Formula IV)

15. The process of claim 14, wherein the aprotic conditions comprise triethylamine in dichloromethane.

16. The process of claim 14, wherein the aprotic conditions further comprise 1-propanephosphonic anhydride in ethyl acetate.

17. The process of claim 16, wherein the aprotic conditions comprise incubating the compound of Formula IV with 4-(aminomethyl)benzonitrile hydrochloride and 1-propanephosphonic anhydride at a temperature of about 5° C. to about 39° C.

18. The process of claim 1, wherein the compound of Formula I is selected from the group consisting of:

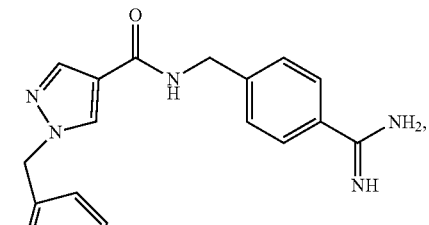

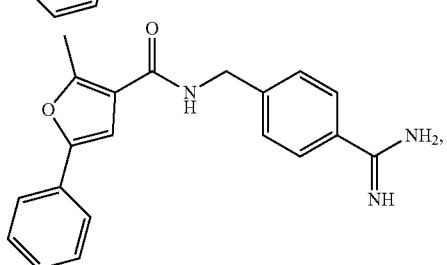

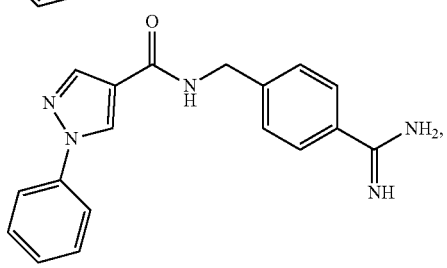

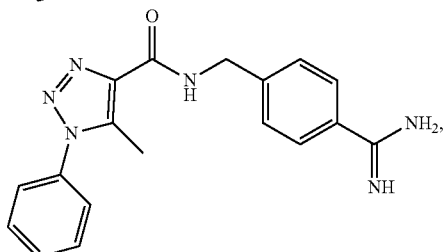

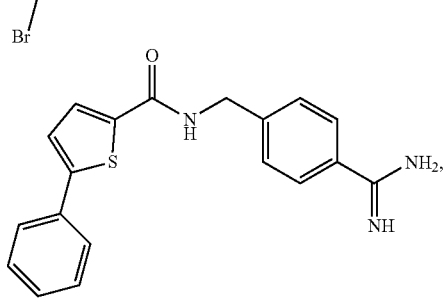

-continued

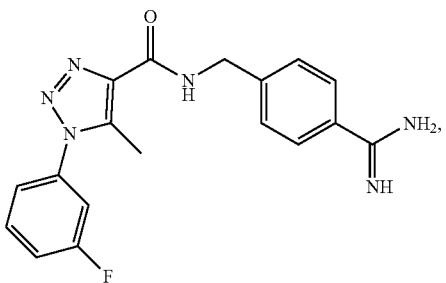

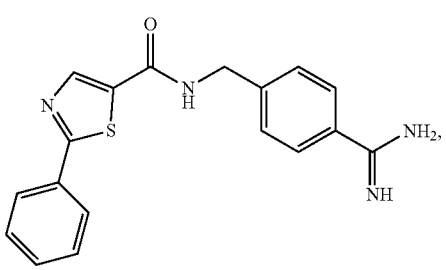

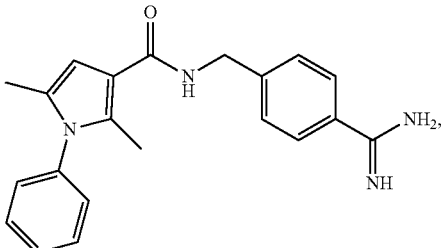

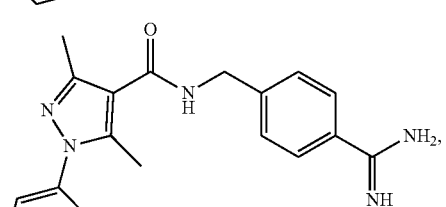

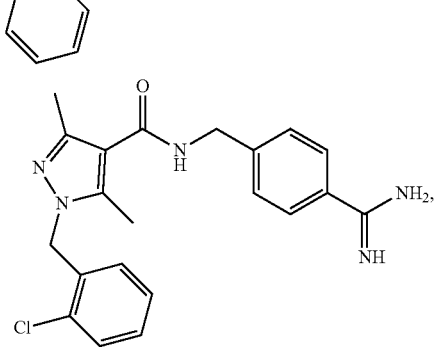

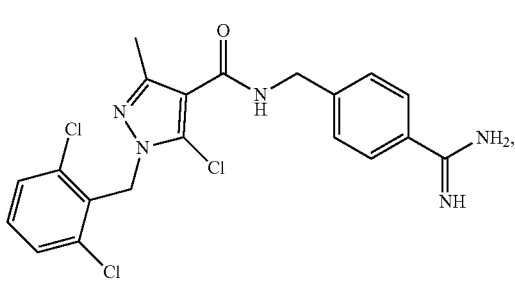

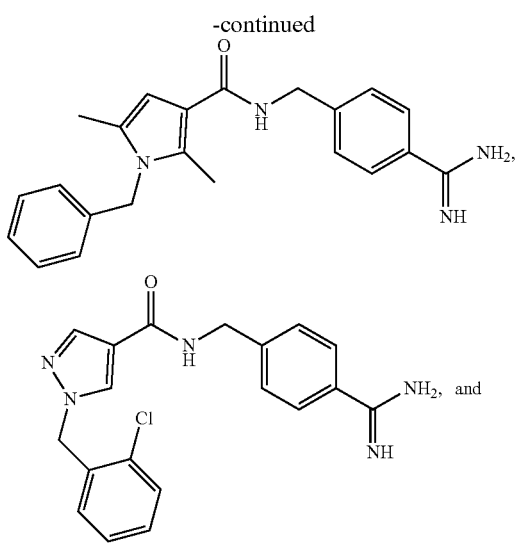
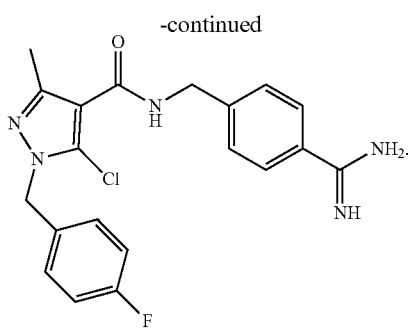
19. The process of claim 1, wherein the compound of Formula I is 1-benzyl-N-(4-carbamimidoylbenzyl)-1H-pyrazole-4-carboxamide or a salt thereof.
20. The process of claim 19, wherein the compound of Formula I is 1-benzyl-N-(4-carbamimidoylbenzyl)-1H-pyrazole-4-carboxamide acetate.
* * * * *